United States Patent
McGrath

(10) Patent No.: US 6,391,860 B1
(45) Date of Patent: May 21, 2002

(54) METHOD FOR PREPARATION AND USE OF PASTE FORMED BY CONTROLLED REACTION OF SUCRALFATE WITH HYDROCHLORIC ACID

(76) Inventor: Patrick D. McGrath, 1263 Kings Rd., Morgantown, WV (US) 26505

( * ) Notice: Subject to any disclaimer, the term of this patent is extended or adjusted under 35 U.S.C. 154(b) by 0 days.

(21) Appl. No.: 09/391,922

(22) Filed: Sep. 9, 1999

(51) Int. Cl.⁷ .......................... A61K 31/70; C07H 1/00
(52) U.S. Cl. .......................................... 514/53; 536/18.5
(58) Field of Search ............................. 514/53; 536/18.5

(56) References Cited

U.S. PATENT DOCUMENTS 5,321,013 A * 6/1994 Zagnoli et al. ................ 514/53
5,977,087 A * 11/1999 Pehrson, Sr. et al. ......... 514/53

* cited by examiner

*Primary Examiner*—Elli Peselev

(57) ABSTRACT

Disclosed is a sucralfate composition which is employed in the treatment of lesions. The composition is formed by the reaction between sucralfate and hydrochloric acid prior to dosing under controlled conditions which limit the reaction to an incomplete stage. The present invention contemplates various methods of achieving this incomplete reaction. In one example, a volume of sucralfate is mixed with a volume of hydrochloric acid. In additional examples, the sucralfate is first wetted in water before being mixed with the hydrochloric acid. Still yet another example involves mixing a volume of sucralfate powder with a powdered excipient before being mixed with the hydrochloric acid.

8 Claims, No Drawings

METHOD FOR PREPARATION AND USE OF PASTE FORMED BY CONTROLLED REACTION OF SUCRALFATE WITH HYDROCHLORIC ACID

BACKGROUND OF THE INVENTION

1. Field of the Invention

The present invention relates to sucralfate paste for use in treating mucosal lesions, and more particularly pertains to a sucralfate paste which is created through an incomplete reaction with acid prior to administration to a patient.

2. Description of Related Art

The use of sucralfate for the treatment of ulcers is known in the art. For example, in his letter to the editor in *American Family Physician*, January 1995, B. C. Demoss, M.D. contemplates the use of sucralfate tables (Carafate) in treating aphthous ulcers.

Sucralfate gel suspensions have also been employed as an antiulcerative drug. See S. Rossi et al., *Rheological Study of Sucralfate Humid Gel: a Contribution to the Comprehension of its Stability Properties*, Eur. J. Pharm. Biopharm. 1992:38:78–81.

The use of sucralfate gels as an ulcer healing drug has been detailed in other journals as well. See M. Guslandi et al., *Effect of a Gel Formulation of Sucralfate on Gastric Microcirculation*, J. Int'l Med. Res. 1993;21: 47–50; see also M. Miglioli, *Prevention with Sucralfate Gel of NSAID-Induced Gastroduodenal Damage in Arthritic Patients*, Am. J. Gastroenerology, Vol. 91, No. 11, 1996; D. Vaira, *Gastric Retention of Sucralfate Gel and Suspension in Upper Gastrointestinal Diseases*, Aliment Pharmacol Ther. 1993;7:531–535.

Lastly, U.S. Pat. No. 3,432,489 to Yoshihiro et al. discloses a disaccharide polysulfate-aluminum compound for use as a peptic ulcer inhibitor.

None of these disclosures, however, contemplates the advantageous effects of administration of sucralfate only after controlled incomplete reaction with acid. A result of this process is the production of a paste which is suitable for use without further pharmaceutical processing and which is fully biologically active at the time of application.

Consequently, it can be appreciated that there exists a continuing need for new and improved sucralfate compositions which can be used for the treatment of oral lesions. In this regard, the present invention substantially fulfills this need.

BRIEF SUMMARY OF THE INVENTION

The general purpose of the present invention is to provide a compound which is especially effective in treating lesions.

To attain this, the present invention essentially comprises a compound consisting essentially of sucralfate incompletely dissolved within an acid.

It is therefore an object of the present invention to provide a novel sucralfate composition for the treatment of oral lesions.

It is another object of the present invention to provide a sucralfate paste which is created by the incomplete reaction of sucralfate with an acid.

It is a further object of the present invention to provide an acid activated product for greater efficiency in controlling lesions.

An even further object of the present invention is to provide efficient methods of producing the advantageous paste of the present invention.

Lastly, it is an object of the present invention to provide a method of treating open oral lesions comprising the following steps. First, providing approximately 5 grams of sucralfate and between 2 and 8 millimoles of HCl in a concentration greater than or equal to 0.1N. Thereafter, reacting the sucralfate within the HCl in a controlled manner whereby the sucralfate is polymerized but the complete dissolution of the sucralfate is prevented. Next, triturating the mixture into a smooth mass of paste and rinsing the resulting paste of excess acid. Finally, applying a portion of the paste to an open oral lesion.

It is therefore an object of the present invention to provide a sucralfate composition for the treatment of oral lesions.

DETAILED DESCRIPTION OF THE INVENTION

The present invention relates to a sucralfate composition which is employed in the treatment of lesions. The composition is formed by the incomplete reaction between sucralfate and hydrochloric acid (HC1). The present invention contemplates various methods of achieving this incomplete reaction. In one example, a volume of sucralfate is mixed with hydrochloric acid of a select concentration. In additional examples, the sucralfate is first wetted in water before being mixed with the hydrochloric acid. Still yet another example involves mixing a volume of sucralfate powder with a powdered excipient before being mixed with the hydrochloric acid. The remaining detailed description provides more complete examples of sucralfate compositions, as well as their method of manufacture.

Sucralfate is an aluminum hydroxide salt of sucrose octasulfate. It is soluble in strong acid and strong alkali but is insoluble in most polar and non-polar solvents. Sucralfate is known to react with hydrochloric, sulfuric and other acids to form an amorphous paste. The present invention concerns the discovery that healing of oral mucosal lesions can be greatly accelerated if sucralfate is administered as a paste rather than a slurry. Although oral lesions are specified, the compound of the present invention can also be used for the treatment of lesions of the skin, esophagus, rectum, or any other like tissues.

The paste of the present invention is prepared by the incomplete reaction of sucralfate with acid, such a hydrochloric or sulfuric acid. By virtue of the incomplete reaction, no further pharmaceutical processing steps are needed. The incomplete reaction yields a fully biologically active compound.

The incomplete reaction is achieved through providing enough acid to produce significant sucralfate polymerization, while at the same time restricting the total acid availability so as to prevent complete dissolution of the drug. Experimentation has revealed that it is ideal to react approximately 5 grams of sucralfate with between 2 and 8 millimoles of HCl at a concentration of greater than or equal to 0.1N. Larger volumes of more concentrated acid, however, can also be used. Further, greater quantities of sucralfate and HCl can be employed to yield larger quantities of paste.

For example, 1.0 HCl can be employed in producing the desired compound. When 1.0N HCl is employed the surface area of contact between the sucralfate and acid must be increased to prevent an initial polymerization reaction at the surface of the powdered sucralfate from slowing the rate of polymerization deeper within the powdered sucralfate. This is achieved by first wetting the sucralfate within a volume of water to produce a slurry. Thereafter, the slurry is reacted with the 1.0N HCl.

In another example, the surface area of contact is increased by employing a powdered pharmaceutical excipient to include: povidone (PVP), talc, or others. Thereafter, the resulting powdered mixture is reacted with the 1.0N HCl. Other examples include an active agent composition with the excipient powder. Such active agents may include local anesthetics, antibiotics or compound stabilizers. Through the use of such active agents, beneficial results, beyond the specific activity of sucralfate can be achieved.

Whichever method of producing the paste compound of the present invention is utilized, subsequent transfer to an affected region can be achieved in any number of ways. Paste may be applied by direct transfer from finger to lesion, or via an applicator of plastic or other suitable material. Additionally, transfer may be facilitated by the transfer of a portion of paste first to the tip of the tongue, with subsequent transfer from the tongue to an oral lesion.

A kit designed to facilitate the preparation, dispensing and use of sucralfate paste may be created by incorporation of various applicators along with measured quantities of acid and with sucralfate powder premeasured into a vessel. The vessel could be used for both executing the acid reaction and the dispensing of the resulting medication.

Below are more specific examples of the sucralfate paste of the present invention:

EXAMPLE 1

Two commercially available sucralfate 1 gram tablets (Carafate™) were covered with 0.1 N HCl and stirred to obtain a mass of paste. The acid was decanted and replaced with another volume of 0.1N HCl. The paste ball was manually triturated to create a smooth paste. In this case, the stirring instrument was a rounded cylinder as might be used for a pipette tip, and this instrument was used to mill the paste ball both with a typical ointment trituration method and by rolling the paste between the instrument and the side of the vessel to produce the sheering action expected of a roller mill. In this example, a firm paste ball was formed without significant softening of the paste beyond its initial relatively stiff appearance.

This paste was provided to a volunteer suffering from a painful oral canker sore. The paste was applied once at bedtime leading to complete resolution of the sore overnight.

EXAMPLE 2

Two commercially available sucralfate 1 gram tablets (Carafate™), were covered with tap water and allowed to swell and disintegrate through the tablet's inherent absorptive reaction with acid free water. Remaining large tablet particles were broken by trituration. To the resulting slurry about 0.5ml 1.0N HCl was added with stirring until individual particles of paste appeared, these aggregating into a single mass with continued stirring and milling. The excess fluid was decanted and discarded, the paste was washed with water, the rinse then being discarded. The paste mass thus formed was of a smoother, less viscous character than that of Example 1. The paste was kept covered with water for three days to prevent drying, this water cover causing no significant change in the initial paste characteristic.

This paste was provided to a volunteer who was a chronic suffer from canker sores. The most recent episode was described as two lesions, both of a duration about 3 weeks and both resistant to three weeks treatment with available remedy options such as lysine tablets and various gargles. One lesion was described as large and very painful relative to typical lesions experienced by this volunteer. The paste was applied to both lesions twice on the first day, once in early evening and once at bedtime. Because of difficulty placing the paste via finger tip and because of the pain resulting from attempting to touch the area with a plastic applicator, this volunteer was instructed to apply a portion of the paste to the tip of the tongue, with subsequent transfer of the paste to the lesion by touching the tongue to the lesion. This instruction resulted in pain free transfer of a significant layer of paste to both lesions. By the next morning the smaller of the two lesions was noted to be absent. The larger of the two lesions was still present but smaller and pain free. This large lesion, which had resisted healing for three weeks prior was completely absent by the third day with additional application at bedtime on the second day.

EXAMPLE 3

Five 1 gram sucralfate tablets (Carafate™) were ground to a fine powder and covered with water to form a thick slurry. About 2 ml 1.0N HCl was added in small portions until formation of a smooth paste, excess was then decanted. The paste was then washed with water (simple tap water in this case) with excess discarded. By drop wise addition of additional 1.0N HCl, continued softening of the paste was caused until a very smooth paste was formed. This paste was transferred to a 15 gram ointment jar, covered with water and sealed tightly.

This paste was provided to a volunteer. Application of the paste to a single oral lesion was effected by first placing an amount on the tip of the tongue at bedtime, with complete healing of the lesion reported in the morning.

EXAMPLE 4

Five 1 gram sucralfate tablets (Carafate™) were ground to fine powder and reacted incrementally with 0.15 N HCL prepared freshly from 1.0 N HCl. Initially it was noted that the crushed sucralfate tablets demonstrated a talc-like resistance to wetting which could be overcome by control of the volumes initially introduced. At 10 ml increments, up to 30 ml, the sucralfate powder was suspended but did not form a paste. After addition of 30 ml 0.15 N HCl, pH was recorded by calomel electrode to be about 3.5. Further addition of 0.15 N HCl up to a final volume of 40 ml resulted in sucralfate paste formation and a precipitous drop in pH of the surrounding fluid to about pH 1.5. The paste formed was of sufficient viscosity to allow decanting of the surrounding fluid and washing of the paste with distilled water 2–5 mL which could be decanted or allowed to remain over the paste, preventing desiccation.

EXAMPLE 5

A series of pastes were formed, each with five 1 gram sucralfate tablets disintegrated in a 15 gram ointment jar by reaction with water added in an amount sufficient to cover the tablets without excess. Tablet disintegration with the formation of a thick slurry was efficiently assured by shaking the tightly closed ointment jars after allowing the tablets to absorb water for about five minutes. To each ointment jar was added various volumes of acid measured via disposable pipettes, these volumes being either 2,4, 6, or 8 ml of 1.0 N HCl. Pastes formed with less than 8 ml 1.0 N HCl were adequate, with increased acid producing a thinner paste. With 8 ml of 1.0 N HCl, the reaction with sucralfate involved not only paste formation but significant sucralfate dissolution. Dissolution of sucralfate caused significant reduction in the amount of paste available. The paste that was available was very thin and might be suitable for use under certain circumstances. In each case, the paste was found to be formed with no agitation other than that executed by shaking the closed ointment jar. However, the paste formed was found to be smoother if milled or manually triturated.

EXAMPLE 6

A series of pastes were formed, each with five grams of sucralfate powder for compounding. To 15 gram ointment jars, 5 grams of sucralfate powder was weighed and 1.0N HCl was added in amounts of 2, 4 or 6 ml measured via accurate pipette. In each system an identical reaction was recorded. In each system an identical excessively stiff paste ball was formed. Continued manual milling did not cause paste softening even in those systems with as much as 6 ml acid. The paste thus formed would be difficult to use in that a single portion of the paste would be difficult to separate and the transfer to a lesion would be uncertain. The paste thus formed is of a consistency like wax used to cover dental braces. This method of compounding would not be recommended for easy transfer to a mouth lesion, however, it could be suitable for formation of a thick, waxy paste which could be applied in place of dental wax.

EXAMPLE 7

A series of pastes were formed, each with five grams of sucralfate powder for compounding. To 15 gram ointment jars, 5 grams of sucralfate powder was weighed. In contrast to Example 6, to this powder was added a sufficient amount of water to form a thick slurry (about 4 ml). It is noted that unlike crushed commercially available sucralfate tablets (Carafate™ 1 gram tablets) the sucralfate powder did not demonstrate the talc-like resistance to wetting. After initial formation of a slurry, 1.0N HCl was added in amounts of 2, 4, or 6 ml. The pastes thus formed were significantly different from the pastes of Example 6 and were suitable for potential transfer to lesion such as a mouth sore. These pastes were similar to those described in Example 5 in that additional 1.0N HCl resulted in a thinner paste.

This detailed description has been provided only for illustrative purposes. It is recognized that other embodiments may be articulated without departing from the objects and scope of the present invention. Any such modifications and variations are meant to be within the scope of the invention as contained within the following claims.

What is claimed as being new and desired to be protected by Letters Patent of the United States is as follows:

1. A method of treating open oral lesions comprising the following steps:
   providing approximately 5 grams of sucralfate;
   providing between 2 and 8 moles of HCl in a concentration greater than or equal to 0.1N;
   reacting the sucralfate within the HCl in a controlled manner whereby the sucralfate is polymerized but the complete dissolution of the sucralfate is prevented;
   triturating the resulting sucralfate paste into a smooth mass;
   applying a portion of the paste to an open oral lesion.

2. A method of treating open oral lesions comprising the following steps:
   providing a volume of sucralfate;
   providing a volume of HCl;
   wetting the sucralfate in an amount of water sufficient to produce a slurry;
   reacting the sucralfate slurry within the HCl whereby the sucralfate is polymerized but the complete dissolution of the sucralfate is prevented;
   triturating the resulting sucralfate paste into a smooth mass;
   applying the paste to an open oral lesion.

3. A method of treating open oral lesions comprising the following steps:
   providing a volume of powdered sucralfate;
   providing a volume of an inert powdered tableting excipient;
   mixing the powdered sucralfate with the excipient to produce a sucralfate-excipient powder;
   providing a volume of HCl;
   reacting the surcalfate-excipient with the HCl whereby the sucralfate is polymerized but the complete dissolution of the sucralfate is prevented;
   triturating the resulting sucralfate paste into a smooth mass;
   applying a portion of the paste to an open oral lesion.

4. The method as described in claim 3 wherein:
   an active agent is included with the excipient powder.

5. The method as described in claim 4 wherein:
   the active agent is a local anesthetic.

6. The method as described in claim 4 wherein:
   the active agent is an antibiotic.

7. The method as described in claim 4 wherein:
   the active agent is a stabilizing composition.

8. A kit for treatment of lesions of the skin, esophagus or rectum, comprising, in combination:
   a vessel;
   various applicators;
   an amount of sucralfate premeasure power in the vessel; and
   a measured quantity of HCL acid for incomplete reaction with the sucralfate power in the vessel, the vessel being used for executing the acid reaction and for dispensing of the resulting sucralfate paste.

* * * * *

UNITED STATES PATENT AND TRADEMARK OFFICE
CERTIFICATE OF CORRECTION

PATENT NO. : 6,391,860 B1
DATED : May 21, 2002
INVENTOR(S) : Patrick D. McGrath

It is certified that error appears in the above-identified patent and that said Letters Patent is hereby corrected as shown below:

Column 5,
Line 51, delete "moles" and insert therefor -- millimoles --.

Signed and Sealed this

Twenty-third Day of September, 2003

JAMES E. ROGAN
*Director of the United States Patent and Trademark Office*